(12) United States Patent
Brandenburger et al.

(10) Patent No.: US 11,464,707 B2
(45) Date of Patent: Oct. 11, 2022

(54) CONNECTOR FOR A MEDICAL PACKAGE CONTAINING A LIQUID

(71) Applicant: FRESENIUS KABI DEUTSCHLAND GMBH, Bad Homburg (DE)

(72) Inventors: Torsten Brandenburger, Reichelsheim (DE); Stefan Schwerer, Florstadt (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 270 days.

(21) Appl. No.: 16/339,060

(22) PCT Filed: Oct. 6, 2017

(86) PCT No.: PCT/EP2017/075525
§ 371 (c)(1),
(2) Date: Apr. 3, 2019

(87) PCT Pub. No.: WO2018/065596
PCT Pub. Date: Apr. 12, 2018

(65) Prior Publication Data
US 2020/0046608 A1 Feb. 13, 2020

(30) Foreign Application Priority Data
Oct. 8, 2016 (DE) ..................... 10 2016 012 059.2

(51) Int. Cl.
*A61J 1/20* (2006.01)
*A61J 1/14* (2006.01)
*A61J 1/10* (2006.01)

(52) U.S. Cl.
CPC .............. *A61J 1/2048* (2015.05); *A61J 1/10* (2013.01); *A61J 1/1406* (2013.01); *A61J 1/1412* (2013.01);

(Continued)

(58) Field of Classification Search
CPC ...... A61J 1/2048; A61J 1/1475; A61J 1/1412; A61J 1/10; A61J 1/201; A61J 1/1406; A61J 1/2089; B61D 51/002
See application file for complete search history.

(56) References Cited

U.S. PATENT DOCUMENTS 2,804,224 A * 8/1957 Barton .................. A61J 1/1406
215/247
4,207,988 A * 6/1980 Prouty .................. A61J 1/1406
215/232
(Continued)

FOREIGN PATENT DOCUMENTS

CN 1407879 A 4/2003
CN 1795026 A 6/2006
(Continued)

OTHER PUBLICATIONS

EIC Search Report (dated Jun. 7, 2022). (Year: 2022).*
Chinese Office Action, dated Dec. 20, 2021, 18 Pages.

*Primary Examiner* — Ariana Zimbouski
(74) *Attorney, Agent, or Firm* — Occhiuti & Rohlicek LLP (57) ABSTRACT

The invention relates to a connector for a medical package containing a liquid. The connector comprises a lower section which has a connecting piece for a container of said medical package and a passageway which is closed by a septum, as well as an upper section which is provided with a cap that covers the septum and can be broken off, said septum having, on a top side, a plurality of connections in the form of elevations, for a spike and/or for a needle.

17 Claims, 7 Drawing Sheets

(52) U.S. Cl.
CPC ............. *A61J 1/1475* (2013.01); *A61J 1/201* (2015.05); *A61J 1/2089* (2013.01)

(56) References Cited

U.S. PATENT DOCUMENTS

| | | | | |
|---|---|---|---|---|
| 4,501,372 | A * | 2/1985 | Hansen | B65D 51/002 215/247 |
| 6,162,206 | A * | 12/2000 | Bindokas | A61J 1/2096 604/533 |
| 6,571,971 | B1 * | 6/2003 | Weiler | B65D 51/20 215/247 |
| 7,425,209 | B2 | 9/2008 | Fowles et al. | |
| 2005/0137566 | A1 | 6/2005 | Fowles et al. | |
| 2006/0282061 | A1 * | 12/2006 | Domkowski | A61J 1/1406 604/408 |
| 2007/0066941 | A1 | 3/2007 | Tezuka et al. | |
| 2008/0009783 | A1 * | 1/2008 | Branderburger | A61M 39/20 604/30 |
| 2008/0262466 | A1 | 10/2008 | Smith et al. | |
| 2010/0059474 | A1 * | 3/2010 | Brandenburger | A61J 1/1418 215/316 |
| 2011/0245796 | A1 * | 10/2011 | Brandenburger | A61J 1/18 604/414 |
| 2013/0333796 | A1 * | 12/2013 | Py | B65D 51/002 141/1 |
| 2014/0170594 | A1 * | 6/2014 | Larson | A61M 5/24 433/90 |
| 2014/0224356 | A1 * | 8/2014 | Hatton | B65D 47/2031 137/522 |
| 2015/0164745 | A1 * | 6/2015 | Gobbi Frattini | B65D 51/002 604/407 |

FOREIGN PATENT DOCUMENTS

| | | |
|---|---|---|
| CN | 104334213 B | 10/2018 |
| DE | 2844206 A1 | 4/1980 |
| DE | 195 00 459 | 7/1996 |
| DE | 19500459 A1 | 7/1996 |
| DE | 10 2008 060864 | 6/2010 |
| DE | 102008060864 A1 | 6/2010 |
| JP | 2005110992 A | 4/2005 |
| WO | 03/013972 A1 | 2/2003 |
| WO | WO03/013972 | 2/2003 |
| WO | 2016/156242 A1 | 10/2016 |
| WO | WO2016/156242 | 10/2016 |
| WO | WO 2016/196632 * | 12/2016 |

* cited by examiner

CONNECTOR FOR A MEDICAL PACKAGE CONTAINING A LIQUID

CROSS REFERENCE TO RELATED APPLICATIONS

This application is the national phase under 35 USC 371 of international application no. PCT/EP2017/075525, filed Oct. 6, 2017, which claims the benefit of the priority date of German Application No. 10 2016 012 059.2 filed Oct. 8, 2016. The contents of the aforementioned applications are incorporated herein by reference in their entireties.

FIELD OF THE INVENTION

The invention relates to a connector for a medical package containing a liquid. The invention relates in particular to a connector which comprises a septum and which is connectable or connected to a bag containing a medical liquid.

BACKGROUND OF THE INVENTION

Connectors comprising a septum for filling or emptying medical packages are known. In particular, there are infusion bags, transfusion bags or enteral bags which comprise a connector with a septum, which septum can be pierced by a spike or a needle. For example, an active substance can be delivered to the bag via a syringe equipped with a needle. The bag can be emptied via tubing connected to the spike.

The laid-open publication WO 2004/084793 A1 (Fresenius Kabi Deutschland GmbH) discloses a medical package. In one embodiment, a bag for a medical liquid comprises two connectors. One connector is provided, for example, for injection of an active substance. A further connector is provided for withdrawal of the contents of the bag. The connectors each comprise a septum, which is covered by a cap that can be broken off.

OBJECT OF THE INVENTION

Against this background, the object of the invention is to make available a connector that can be used more flexibly.

SUMMARY OF THE INVENTION

The object of the invention is achieved by a connector as claimed in claim 1, by a medical package as claimed in claim 14, provided with a connector, and by a septum as claimed in claim 15.

Preferred embodiments and developments of the invention can be gleaned from the subject matter of the dependent claims, the description and the figures.

The invention relates first to a connector for a medical package containing a liquid.

The medical package comprises a container in which the medical liquid is stored. The connector serves in particular for filling the container, delivering or supplementing a liquid (e.g. an active substance) and/or for emptying the container. The container of the package is in particular configured as a bag or bottle, e.g. as a plastic bottle.

The connector comprises a lower part which has a connecting piece, for a container of the medical package, and a passage. The lower part is in particular at least partially tubular and is connected, preferably adhesively bonded or welded, to the container via the connecting piece. Liquid can pass into the connector through the passage.

In one embodiment, the connecting piece of the lower part has substantially a ship shape. In this way, it is possible to produce a fluid-tight and also mechanically stable connection to a container configured as a bag.

The passage is closed by a septum. A septum is understood as a self-closing, reclosable elastomer element that can be pierced with a spike and/or also with a needle in order to withdraw or deliver liquid. After the spike and/or the needle has been pulled out, the septum closes independently.

Polyisoprene can be used, for example, as elastomer material.

The connector further comprises an upper part provided with a cap that covers the septum and that can be broken off. The septum is therefore accessible only after the cap has been broken off. The cap makes it easy to tell whether the connector has already been used. Moreover, the septum can be kept sterile by the cap.

The cap can be configured, for example, as a gripping piece that is flat in part.

The upper part and the lower part are preferably configured as injection-molded components. The upper part is preferably placed onto the lower part.

In particular, the upper part and the lower part are connected to each other by means of a form-fit connection. In one embodiment of the invention, the upper part can be pushed onto the lower part. In an alternative or supplementary embodiment, the upper part and the lower part are cohesively connected, in particular welded or adhesively bonded. In a further embodiment of the invention, upper part and lower part are configured as one piece. It goes without saying that, within the meaning of the invention, the passage can also extend partially through the upper part.

The cap is preferably configured in one piece with the upper part, in which case a predetermined breaking line is formed in particular by an annular reduction of the material thickness between cap and upper part. The upper part serves in particular to receive the cap.

Moreover, as is provided for in one embodiment of the invention, the septum can be enclosed with form-fit engagement between the upper part and the lower part.

According to the invention, the septum comprises a plurality of ports for a spike and/or for a needle. The ports are configured to be suitable for being pierced by a spike, in particular for withdrawal of liquid. However, they can also be pierced by a needle. The ports are preferably configured as elevations on the top side of the septum.

Since a plurality of ports are present, the connector can be used more flexibly. In particular, the connector can be used both to deliver liquid and also to withdraw liquid. As is provided for in one embodiment of the invention, it is possible to do without a second connector on the package.

Moreover, the plurality of ports permits multiple withdrawals with one spike or several spikes, without the same port having to be used several times over.

In particular, the septum comprises at least three ports. In one embodiment, the septum comprises at least three ports for a spike. The ports for a spike preferably comprise a first guide, which is configured for example as a slit or as two slits crossing each other. The slits facilitate or permit the insertion of a spike.

In a development of the invention, the top side of the septum, the side having the ports, is accessible for wiping the ports after the cap has been broken off.

For this purpose, the septum preferably has no deep indentations that would prevent wiping. Moreover, an adjoining edge of the upper part should at most lie slightly higher than the adjoining top side of the septum, in particular at most 1 mm higher.

Preferably, the top side of the septum is substantially flush with an adjoining predetermined breaking line for the cap, or the top side of the septum protrudes above the adjoining predetermined breaking line.

The ports of the septum can thus be easily wiped clean, as may be stipulated despite a preferably sterile state of the ports.

The highest point of the ports preferably lies at most 1 mm below the top side of the cap adjoining the septum. In particular, the highest point of the ports lies on a plane with the adjoining top side of the cap or over said plane.

In one embodiment of the invention, the ports are configured, on their top side, as preferably dome-shaped elevations. The ports are thus more easily accessible, in particular for possible disinfection of the ports by wiping. Moreover, the ports can comprise rings or ring portions, in particular configured as groove or web, which extend at least partially about the puncture site. In this way, the puncture site can be better seen by the user. The puncture site can be still better seen in particular in combination with the crosswise slits.

In a preferred embodiment of the invention, a gap between the cap and the septum is sealed off hermetically by the cap. The septum can thus be sterilized or made available in a sterile state and also remains sterile during handling of the package provided with the connector. A hermetic seal can be provided in particular by the predetermined breaking line between upper part and cap having no openings.

In a development of the invention, the cross section of the passage tapers at least partially from the septum in the direction of the connecting piece. In particular, the internal diameter and/or the external diameter, preferably both internal diameter and external diameter, taper(s) in the direction of the connecting piece.

It is thus easy to make available a connector that is large enough for several ports, in particular several ports for one respective spike.

After the cap has been broken off, the septum preferably has an accessible diameter of more than 10 mm, particularly preferably of more than 12 mm. In the case of a shape that is not a circular cylinder, this is understood as being the greatest diameter.

In one embodiment of the invention, the septum is fixed between the upper part and the lower part by means of a form-fit element. In particular, a form-fit element is provided which radially fixes the septum at the edge. This can be a circumferential web at the edge. In particular, the septum comprises a circumferential T-shaped form-fit element at the edge. On account of the form-fit engagement in the radial direction, the septum cannot be pressed out in the axial direction by the action of force.

In a further embodiment of the invention, the underside of the septum comprises tubular guides, which are each arranged beneath a respective port. These serve in particular as a guide, preferably a second guide, for a respective spike. The underside of the tubular guides is in particular lower than an underside of the form-fit element. Improved guiding for a spike can be obtained in this way. The underside of the tubular guides can form the lowest region of the septum. In one embodiment, the underside of the tubular guides merges flush into an underside of an annular portion of the septum lying internally in relation to the form-fit element. This annular portion can bear on an inner face of the passage in the connector and in so doing can provide improved positioning of the septum.

The invention further relates to a medical package with a container for a liquid, which package is in particular configured as an infusion bag, transfusion bag or enteral bag, or as a bottle containing medical liquid. The medical package comprises at least one embodiment of the above-described connector, which is connected to the container of the medical package via the connecting piece. In particular, the connecting piece is adhesively bonded or welded to the container, which is in particular configured as a bag or bottle.

Moreover, the scope of the invention also covers a septum for an embodiment of the above-described connector and/or of the above-described package. The septum comprises a plurality of ports for a spike and/or for a needle. The ports are configured as elevations, preferably dome-shaped elevations.

BRIEF DESCRIPTION OF THE DRAWINGS

The subject matter of the invention is explained in more detail below on the basis of an illustrative embodiment and with reference to FIG. 1 to FIG. 9 of the drawings.

DETAILED DESCRIPTION OF THE DRAWINGS

Figure 1:
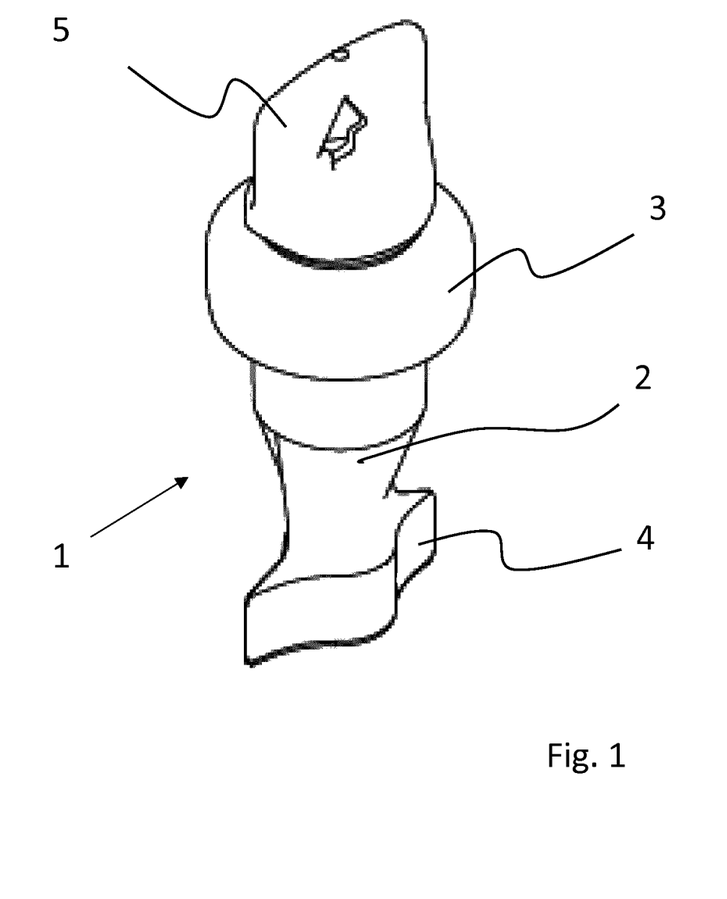
FIG. 1 is a perspective view of an illustrative embodiment of a connector according to the invention.

FIG. 1 is a perspective view of an illustrative embodiment of a connector 1 according to the invention. The connector 1 comprises a lower part 2, and an upper part 3 placed onto the lower part 2. The lower part 2 comprises, at a lower end, a connecting piece 4 for a container 21 of the medical package 20.

In this illustrative embodiment, the connecting piece 4 does not have the shape of a circular cylinder, and instead it has a ship shape, which makes it easier, for example, to attach a container 21 configured as a bag. The connecting piece 4 is welded into the weld seam forming the edge of the bag (see FIG. 9 in this respect). The connecting piece 4 can preferably have a substantial wall thickness, e.g. such that it cannot be pierced by a needle and/or by a spike.

The upper part 3 has a larger external diameter than the adjoining lower part 2 in the region above the connecting piece 4 of the lower part 2. In the case of a shape that is not a circular cylinder, the respectively largest diameter of the two parts to be compared is the diameter in question.

The upper part 3 is moreover provided with a cap 5 which can be broken off and which forms the top portion of the upper part 3. The cap 5 is here configured as a flat gripping piece, the cross section of which changes from a circular shape toward a plate-shaped configuration. The cap 5, connected via a predetermined breaking line 10, can thus be easily broken off from the upper part 3.

In the lower region of circular cross section, the cap 5 has a smaller diameter than the bottom portion of the upper part 3.

The cap 5 constitutes a tamper-evident seal. After the cap 5 has been broken off, the top side 11 of the septum 6 (not seen here) is accessible.

Moreover, an opening configured as an arrow is introduced in the plate-shaped portion of the break-off cap 5, which opening identifies the connector 1 depicted here as a withdrawal connector.

Figure 2:
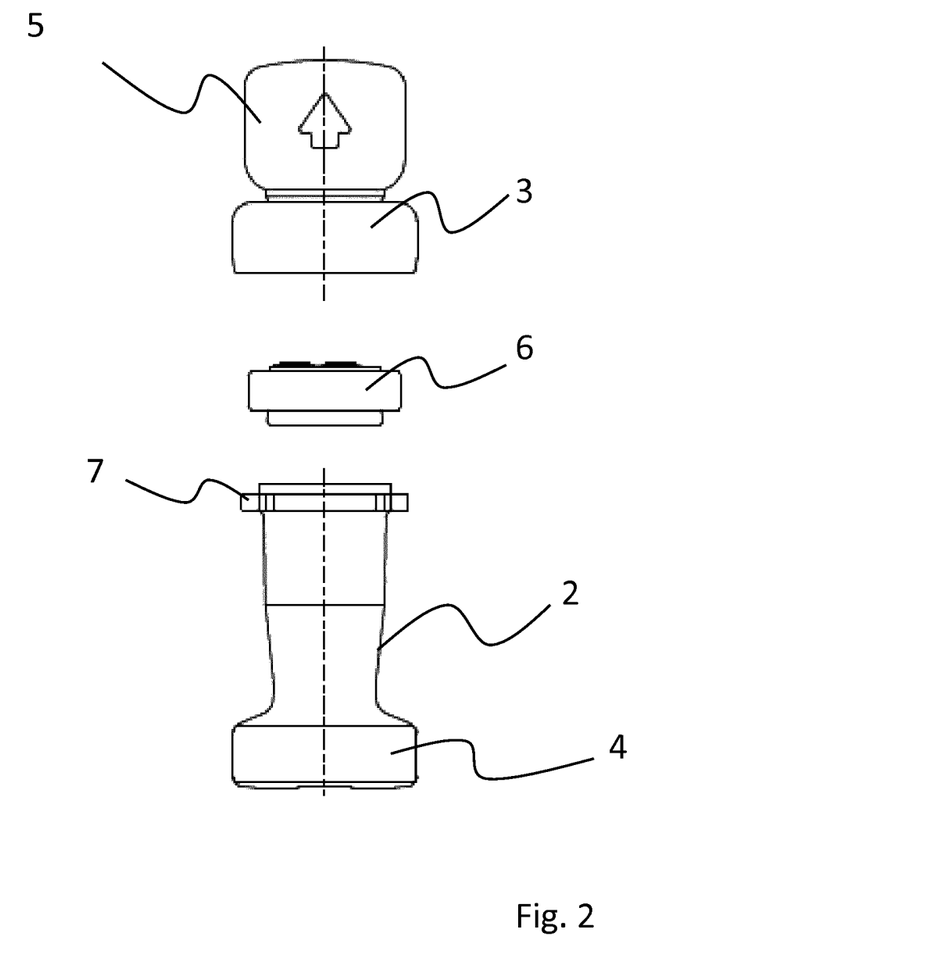
FIG. 2 is an exploded view of the connector shown in FIG. 1.

FIG. 2 is an exploded view of the connector 1 and shows the individual parts of the latter. The connector 1 is formed by the lower part 2, the upper part 3 placed onto the lower part 2, and the septum 6 inserted between the upper part 3 and the lower part 2.

The lower part 2 and the upper part 3 of the connector 1 are here connected to each other by means of a form-fit connection, for example a snap connection. In this illustrative embodiment, the lower part 2 comprises a radially extending collar 7, onto which the upper part 3 is pushed. The septum 6 is thus fixed with form-fit engagement, and preferably also with clamping, between the lower part 2 and the upper part 3. The collar 7 can in this case engage in a recess formed on the inner face of the upper part 3 or can engage behind a projection (not shown in FIG. 2) arranged on the inner face of the upper part 3.

In an alternative or supplementary embodiment (not shown), the upper part 3 and the lower part 2 are welded or adhesively bonded to each other or are configured as one piece.

Figure 3:
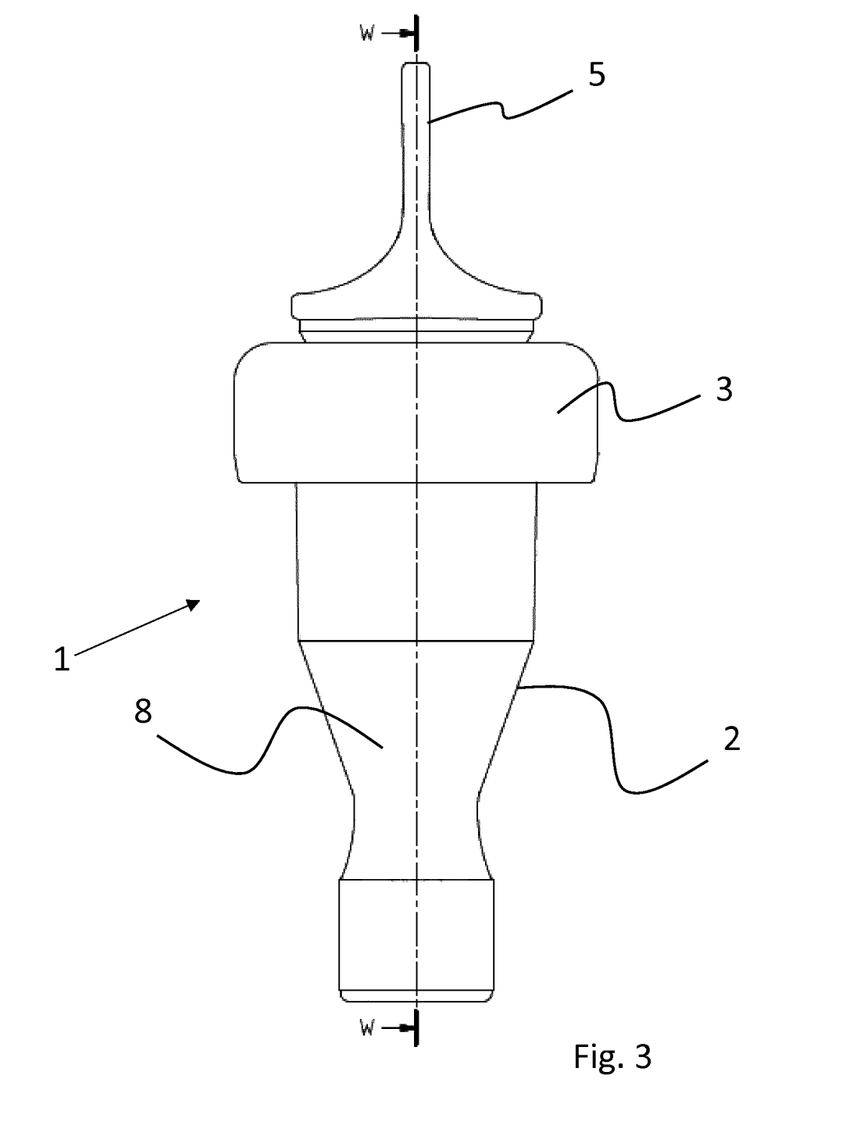
FIG. 3 is a side view and FIG. 4 a sectional view of the connector.

FIG. 3 is a side view of the connector 1 and in particular shows that the cap 5 is configured as a flat gripping piece.

Figure 4:
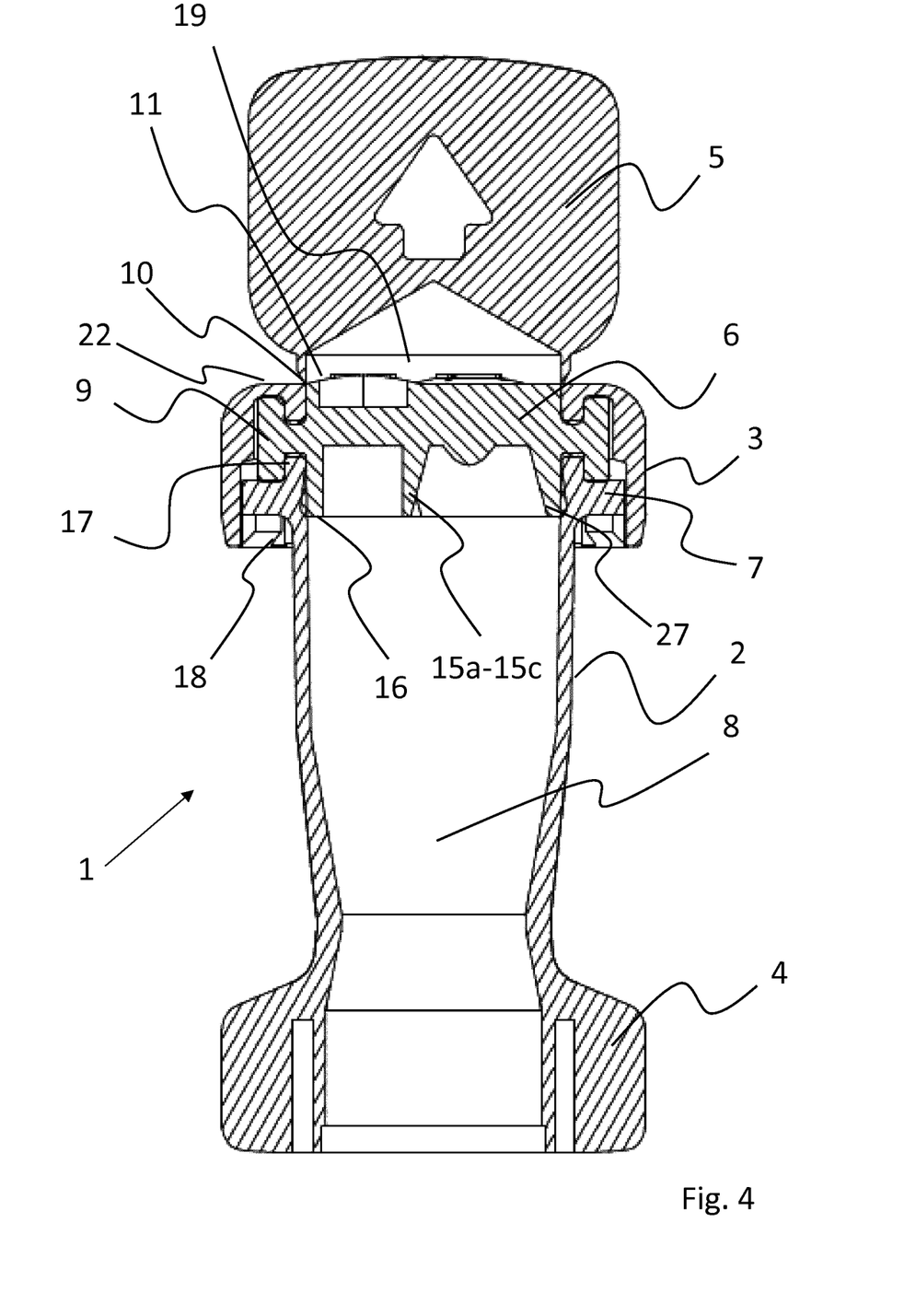

FIG. 4 is a sectional view of the connector 1 along the line W-W, rotated through 90° from FIG. 3.

The lower part 2 has a passage 8 which, starting from the upper part 3, tapers both in external diameter and in internal diameter in the direction of the connecting piece 4.

At its upper end, the passage 8 is closed by the septum 6.

In this illustrative embodiment, the septum 6 is inserted between the upper part 3 and the lower part 2. The septum 6 comprises a T-shaped form-fit element 9 issuing from its edge. An upper arm of the T-shaped form-fit element 9 sits in a corresponding groove of the upper part 3. The lower part 2 comprises, on its top side, a circumferential web 17 extending in the axial direction. A lower arm of the T-shaped form-fit element 9 engages behind the web 17. The elastic septum 6 cannot therefore be pressed out by the action of an axial force.

The top side of the form-fit element 9 lies below the top side 11 of the central portion of the septum 6. Thus, the top side 22 of the upper part 3 can extend over the form-fit element 9 and in so doing lie flush with the adjoining top side 11 of the central portion of the septum 6.

Since the top side 22 of the upper part 3 and the top side 11 of the septum 6 lie approximately on one plane, the top side 11 of the septum 6 is easily accessible after the cap 5 has been broken off and can in particular be easily wiped clean.

In this illustrative embodiment, the underside 16 of the central portion of the septum 6 lies lower than the underside of the T-shaped form-fit element 9.

The cap 5 is connected to the upper part 3 via an annular predetermined breaking line 10. The predetermined breaking line 10 is flush with the adjoining top side 11 of the septum 6. Moreover, the predetermined breaking line 10 directly adjoins the surface 11 of the septum 6 that is accessible after the cap has been broken off.

The top side 11 of the septum 6 lies completely free or substantially completely free after the cap 5 has been removed. The three ports 12*a*, 12*b*, 12*c* and the surfaces present between the ports 12*a*, 12*b*, 12*c* are not covered, e.g. by a housing portion of the connector 1.

The top side 11 of the septum 6 has no depressions. After the cap 5 has been broken off, a relatively smooth surface is thus obtained that is composed of the top side 11 of the septum 6 and the top side 22 of the upper part 3.

Between the cap 5 and the septum 6, a gap 19 is present which is preferably sterilized. Since the predetermined breaking line 10 has no openings, the gap 19 is sealed off hermetically.

In this illustrative embodiment, the connector 1 is assembled by pushing the upper part 3 onto the lower part 2. After the upper part 3 has been pushed on, a circumferential web 18 of the upper part 3 and/or several latching hooks of the upper part 3 (which are not shown in the figures) engage under the circumferential collar 7 of the lower part 2. In an alternative or supplementary embodiment, the collar 7 of the lower part 2 engages in a depression (not shown in the figures) introduced on the inner face of the upper part 3.

Figure 5:
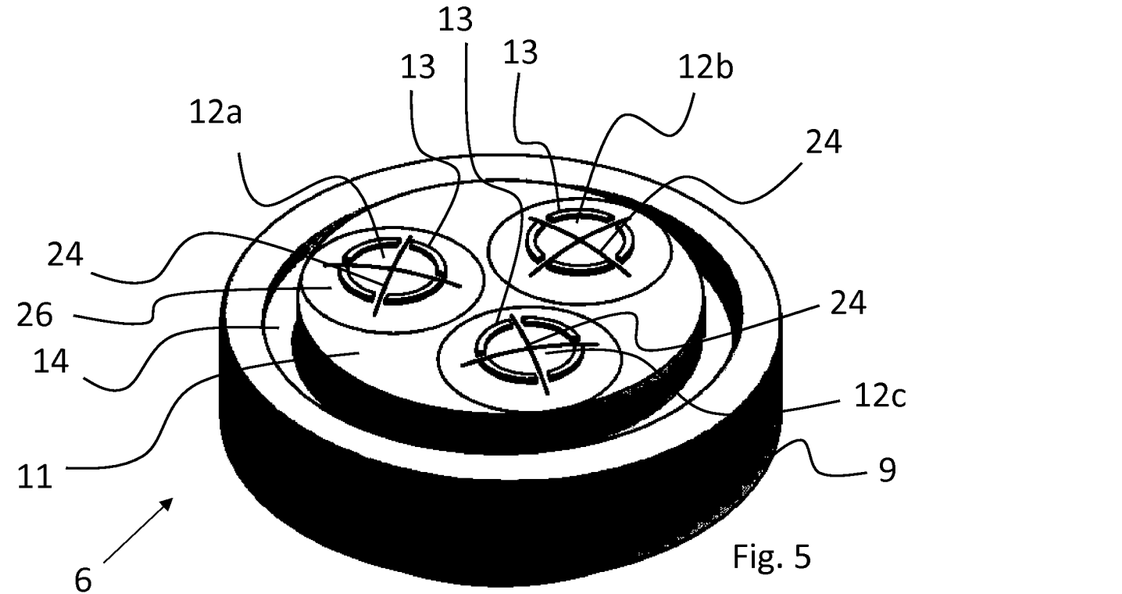
FIG. 5 and FIG. 6 are perspective views of the septum at its top side (FIG. 5) and its underside (FIG. 6), which septum is part of the connector already shown.

FIG. 5 is a perspective detailed view of the septum 6, in which the top side 11 can be clearly seen.

The septum 6 is made of an elastomer material, for example a polyisoprene. The latter can be crosslinked, for example, peroxidically or by means of sulfur bridges.

The figure reveals the circumferential T-shaped form-fit element 9 at the edge, by means of which a groove 14 is formed between the form-fit element 9 and the top side 11. In the assembled state, a corresponding web of the upper part 3 engages in this groove 14.

In this illustrative embodiment, three ports 12*a*-12*c* are present on the top side 11.

The ports 12*a*-12*c* are distributed uniformly at the circumference of the septum. The angle of virtual connecting lines to the center point of the septum 6 is thus approximately 120° in each case. The three ports 12*a*-12*c* form the corners of a triangle, preferably an equilateral triangle.

In this illustrative embodiment, the three ports 12*a*-12*c* are each configured to receive a spike. They each comprise slits 24 formed in a cross shape. The slits 24 serve as a guide for a spike. In this illustrative embodiment, the slits 24 do not extend completely through the septum 6. In another embodiment (not shown here), the slits 24 run the full height of the septum 6.

In an embodiment not shown here, it is possible that a port is not slit and can serve to receive a needle.

The ports 12*a*-12*c* in this illustrative embodiment are configured as dome-shaped elevations. The slits 24 of the ports 12*a*-12*c* intersect in a flattened region of the dome formed by the respective port 12*a*-12*c* (in this connection see also the cross-sectional view shown in FIG. 4).

The puncture regions for the spikes on the top side 11 of the septum 6, which regions are defined by the intersecting slits 24 in the three ports 12*a*-12*c*, are each enclosed by an annular circumferential web 13. In this illustrative embodiment, the web 13 at the same time forms the boundary of the flattened region of the dome. The annular circumferential webs 13 are each interrupted at several places. The slits 24 extend through the interruptions and into the downwardly sloping region 26 of the dome, which is formed by the respective port 12*a*-12*c*.

The geometric configuration shown here permits good accessibility and maneuverability of the puncture sites of the septum 6.

To receive the ports 12*a*-12*c*, the accessible surface 11 of the septum 6 preferably has a diameter of 10 mm to 20 mm, preferably of 12 mm to 16 mm.

The total height of the septum is preferably between 5 mm and 20 mm.

The diameter of the flattened region of the dome, bounded by the annular webs 13, is preferably 2 mm to 5 mm.

Figure 6:
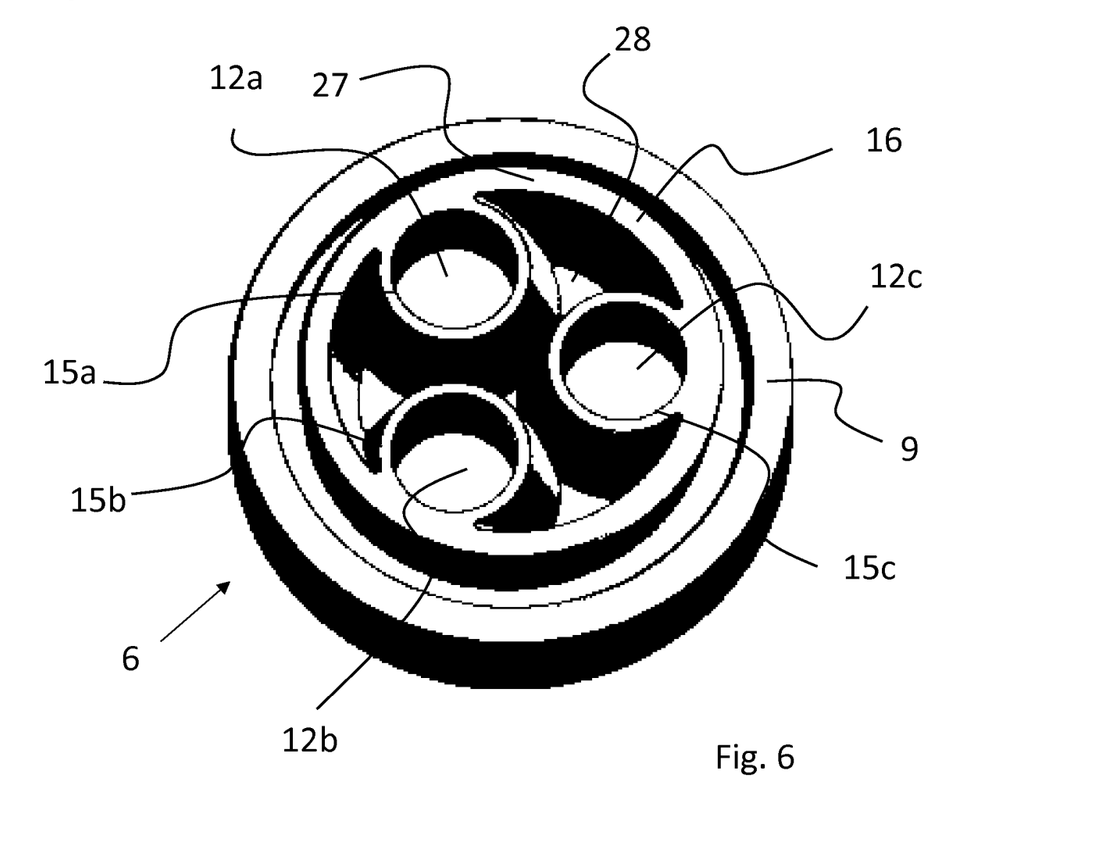

FIG. 6 is a perspective view in which the underside of the septum 6 can be clearly seen.

Tubular guides 15a to 15c, each provided for a respective spike and/or needle, extend beneath the ports 12a to 12c.

The tubular guides 15a to 15c merge at the edge into an annular portion 27 of the septum 6, which annular portion 27 constitutes the underside 16 of the septum 6. In the assembled state, this annular region 27 bears on the inner wall of the passage 8 of the lower part 2.

The tubular guides 15a to 15c preferably have a depth of 1 mm to 6 mm.

The gap 28 between the tubular guides 15a to 15c is not filled with material, such that the septum 6, in the region of the gap 28, has approximately the same thickness as in the region of the ports 12a to 12c.

Since there are no ports located in the region of the gap 28, the gap 28 in an embodiment not shown here can also be filled with material as far as the underside 16.

In the region of the ports 12a to 12c, the thickness of the septum 6 is preferably 1 mm to 5 mm.

Figure 7:
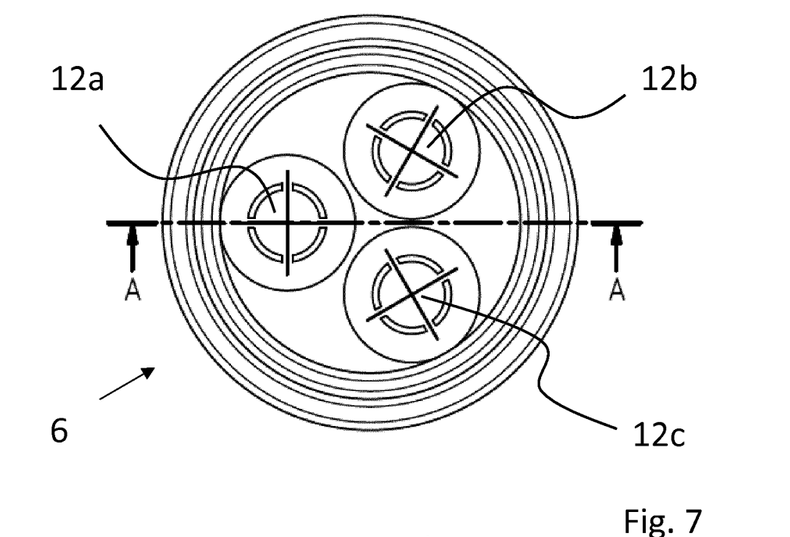
FIG. 7 is a plan view of the top side of the septum.

FIG. 7 is a plan view of the top side of the septum 6 with the three ports 12a to 12c.

Figure 8:
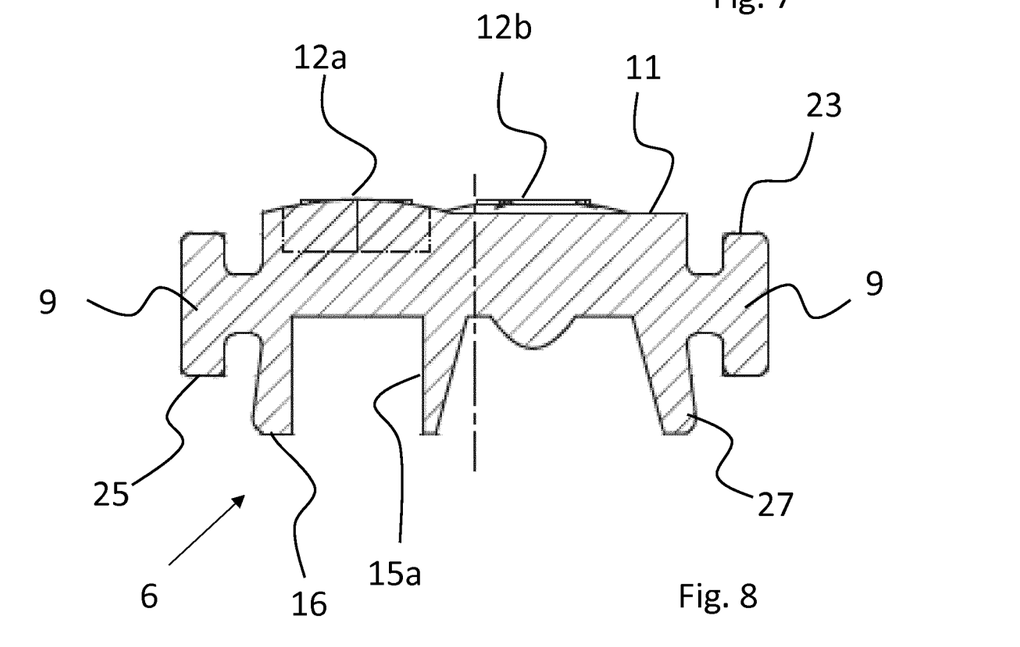
FIG. 8 is a sectional view along the line A-A in FIG. 7.

FIG. 8 is a sectional view of the septum 6 along the line A-A from FIG. 7.

It will be seen in particular how the dome-shaped ports 12a to 12c protrude from the adjoining surface 11 of the septum 6.

The top side 23 of the T-shaped form-fit element 9 lies deeper than the accessible surface of the septum 6 formed by the top side 11.

The underside 25 of the T-shaped form-fit element 9 lies higher than the underside of the annular portion 27, which constitutes the underside 16 of the septum 6. The underside of the annular portion 27 merges flush into the underside of the annular guide 15a.

Figure 9:
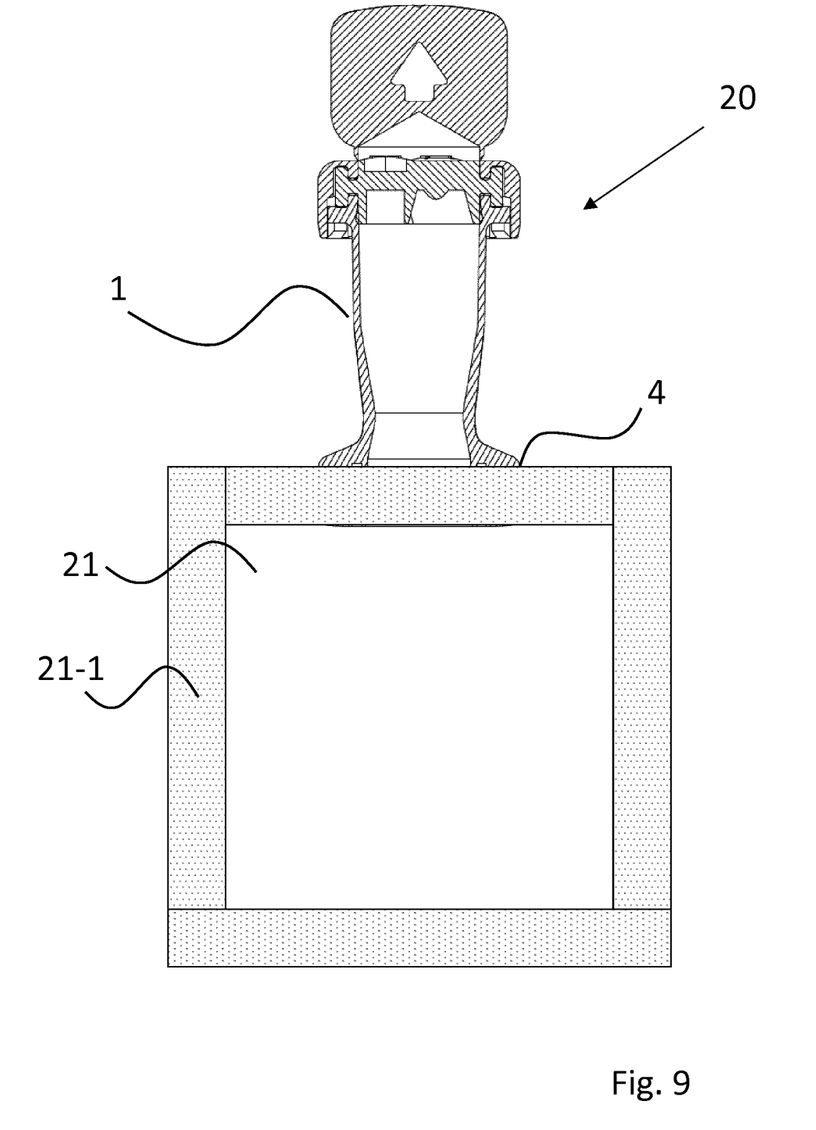
FIG. 9 shows a schematic view of a medical package provided with a connector.

FIG. 9 shows schematically how the connector 1 described above is connected to the container 21 of a medical package 20.

In this illustrative embodiment, the connecting piece 4 of the connector 1 is welded to a container 21 configured as a bag. The connecting piece 4 is welded into the weld seam of the container 21.

By way of the connector 1, liquid can be withdrawn from the container 21 and also delivered to it. The container 21 can also be filled by way of the connector 1, in particular with the upper part 3 not yet fitted.

In the example shown, the container 21 has only a single connector 1. The connector 1 is preferably used only for withdrawal by means of a spike. The connector 1 is in this case a withdrawal connector.

By means of the invention, a connector can be made available that is easy to handle and that permits flexible use.

LIST OF REFERENCE SIGNS

1 connector
2 lower part
3 upper part
4 connecting piece
5 cap (that can be broken off)
6 septum
7 collar
8 passage
9 form-fit element
10 predetermined breaking line
11 top side of the septum
12a-12c port
13 web
14 groove
15a-15c tubular guide
16 underside of the tubular guide and/or of the septum
17 web
18 web
19 gap
20 package
21 container
21-1 weld seam of the container
22 top side
23 top side (of the form-fit element 9)
24 slit
25 underside (of the form-fit element 9)
26 downwardly sloping region
27 annular portion
28 gap

The invention claimed is:

1. A connector for a medical package containing a liquid, said connector comprising:
   a lower part, which has a connecting piece for a container of the medical package, and a passage,
   a septum, which closes the passage of the lower part, and
   an upper part, which is placed onto the lower part and is provided with a cap that covers the septum and can be broken off,
   wherein the septum has, on a top side thereof, a plurality of ports configured as elevations for a spike and/or for a needle, wherein:
   the ports lead into the lower part,
   the ports on the top side of the septum are configured as dome-shaped elevations, and
   each port includes:
      radially-spaced ring portions disposed on the dome-shaped elevations, wherein the radially-spaced ring portions define gaps, and
      a plurality of slits formed within the dome-shaped members, each of the slits extending through one of the gaps.

2. The connector as claimed in claim 1, wherein, after the cap has been broken off, the top side of the septum is accessible for wiping the ports.

3. The connector as claimed in claim 1, wherein at the top side of the septum protrudes above an adjoining predetermined breaking line for the cap.

4. The connector as claimed in claim 1, wherein a gap present between the cap and the septum is hermetically sealed off by the cap and is made available in a sterile state.

5. The connector as claimed in claim 1, wherein a cross section of the passage in the lower part of the connector tapers at least partially from the septum in the direction of the connecting piece.

6. The connector as claimed in claim 1, wherein the connecting piece of the lower part has substantially a ship shape.

7. The connector as claimed claim 1, wherein, after the cap has been broken off, the septum has an accessible diameter of more than ten millimeters.

8. The connector as claimed in claim 1, wherein the septum comprises a form-fit element, which is fixed between the upper part and the lower part of the connector.

9. The connector as claimed in claim 1,
wherein an underside of the septum has tubular guides arranged beneath the ports.

10. The connector as claimed in claim 9, wherein an underside of the tubular guides is lower than an underside of the form-fit element.

11. The connector as claimed in claim 9, wherein an underside of the tubular guides merges flush into an underside of an annular portion of the septum lying internally in relation to the form-fit element.

12. A medical package with a container that is configured as an infusion bag, transfusion bag or enteral bag, or as a bottle containing medical liquid, comprising a connector as claimed in claim 1.

13. The connector as claimed in claim 1, wherein at the top side of the septum is substantially flush with an adjoining predetermined breaking line for the cap.

14. The connector of claim 1, wherein the cap forms a top portion of the upper part.

15. The connector of claim 1, wherein the cap is a tamper-evident seal.

16. The connector of claim 1, wherein the cap is configured to be broken off from the upper part.

17. The connector as claimed claim 1, wherein, after the cap has been broken off, the septum has an accessible diameter of more than twelve millimeters.

* * * * *